United States Patent [19]

Karanewsky et al.

[11] 4,427,665
[45] Jan. 24, 1984

[54] PHOSPHINYLALKANOYL SUBSTITUTED IMINO ACIDS AND THEIR USE IN HYPOTENSIVE COMPOSITIONS

[75] Inventors: Donald S. Karanewsky, Princeton Junction; Edward W. Petrillo, Jr., Pennington, both of N.J.

[73] Assignee: E. R. Squibb & Sons, Inc., Princeton, N.J.

[21] Appl. No.: 379,678

[22] Filed: May 19, 1982

[51] Int. Cl.³ .................... A61K 31/675; C07F 9/32
[52] U.S. Cl. .................................. 424/200; 546/21; 546/22; 546/23; 548/414
[58] Field of Search .................... 546/21, 22, 23; 548/414; 424/200

[56] References Cited

U.S. PATENT DOCUMENTS

| | | | |
|---|---|---|---|
| 4,168,267 | 9/1979 | Petrillo | 260/326.2 |
| 4,256,751 | 3/1981 | Hayashi et al. | 424/258 |
| 4,303,583 | 12/1981 | Kim et al. | 260/239.3 T |
| 4,337,201 | 6/1982 | Petrillo, Jr. | 548/413 |
| 4,344,949 | 8/1982 | Hoefle et al. | 424/258 |
| 4,396,772 | 8/1983 | Petrillo | 548/414 |

FOREIGN PATENT DOCUMENTS 18549 11/1980 European Pat. Off. .
2048863 12/1980 United Kingdom .

*Primary Examiner*—John M. Ford
*Assistant Examiner*—Bernard Dentz
*Attorney, Agent, or Firm*—Lawrence S. Levinson; Stephen B. Davis

[57] ABSTRACT

Phosphinylalkanoyl imino acids of the formula

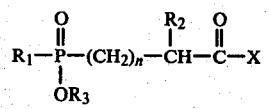

wherein X is tetrahydroisoquinoline carboxylic acid, dihydroindole or dihydroisoindole carboxylic acid are disclosed. These compounds are useful as hypotensive agents due to their angiotensin converting enzyme inhibition activity.

9 Claims, No Drawings

PHOSPHINYLALKANOYL SUBSTITUTED IMINO ACIDS AND THEIR USE IN HYPOTENSIVE COMPOSITIONS

BACKGROUND OF THE INVENTION

Petrillo in U.S. Pat. No. 4,168,267 discloses that various phosphinylalkanoyl substituted prolines are useful as hypotensive agents due to their ability to inhibit the angiotensin converting enzyme.

Petrillo in U.S. patent application Ser. No. 212,911 filed Dec. 4, 1980, now U.S. Pat. No. 4,337,201, discloses that various esters of phosphinylalkanoyl proline and ester and acid forms of phosphinylalkanoyl derivatives of various substituted prolines are useful as hypotensive agents due to their ability to inhibit the angiotensin converting enzyme.

Petrillo in U.S. patent application Ser. No. 323,859 filed Nov. 23, 1981, now U.S. Pat. No. 4,396,772, discloses that various phosphinylalkanoyl substituted amino acids are useful as hypotensive agents due to their ability to inhibit the angiotensin converting enzyme.

Mercaptoacyl derivatives of dihydroisoindole carboxylic acids and tetrahydroisoquinoline carboxylic acids are disclosed as being useful hypotensive agents by Ondetti et al., in U.S. Ser. No. 69,031, filed Aug. 23, 1979. These mercaptoacyl tetrahydroisoquinoline compounds are also disclosed by Portlock in U.K. Application No. 2,048,863 and by Hayashi et al. in U.S. Pat. No. 4,256,751.

SUMMARY OF THE INVENTION

This invention is directed to phosphinylalkanoyl imino acids, esters, and pharmaceutically acceptable salts of the formula $$R_1-\overset{O}{\underset{OR_3}{\overset{\|}{P}}}-(CH_2)_n-\overset{R_2}{\underset{}{\overset{|}{CH}}}-\overset{O}{\overset{\|}{C}}-X. \quad (I)$$

$R_1$ is alkyl, halo substituted lower alkyl, cycloalkyl—$(CH_2)_m$—,

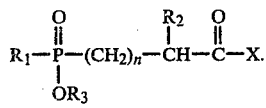

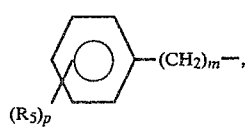

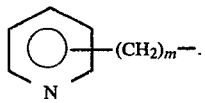

$R_2$ is hydrogen, lower alkyl, halo substituted lower alkyl, benzyl, or phenethyl.

X is

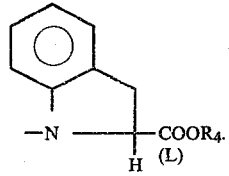

$R_3$ and $R_4$ are independently selected from hydrogen, lower alkyl, benzyl, benzhydryl, and

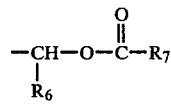

wherein $R_6$ is hydrogen, alkyl, cycloalkyl, or phenyl, and $R_7$ is hydrogen, alkyl, cycloalkyl, lower alkoxy, phenyl, benzyl, phenethyl or $R_6$ and $R_7$ taken together are $-(CH_2)_2-$, $-(CH_2)_3-$, $-CH=CH-$, or

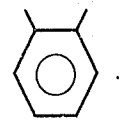

n is zero or one.

$R_5$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy.

p is one, two, or three provided that p is more than one only if $R_5$ is hydrogen, methyl, methoxy, chloro, or fluoro.

m is zero or an integer from 1 to 7.

DETAILED DESCRIPTION OF THE INVENTION

This invention in its broadest aspects relates to the phosphinylalkanoyl imino acid compounds of formula I above, to compositions containing such compounds and to the method of using such compounds as anti-hypertensive agents.

The term alkyl used in defining various symbols such as $R_1$ refers to straight or branched chain hydrocarbon radicals having up to ten carbons, for example, methyl, ethyl, propyl, isopropyl, butyl, isobutyl, t-butyl, pentyl, isopentyl, heptyl, octyl, decyl, etc. The term lower alkyl used in defining various symbols refers to straight or branched chain radicals having up to seven carbons. The preferred lower alkyl groups are up to four carbons with methyl and ethyl most preferred. Similarly the terms lower alkoxy and lower alkylthio refer to such lower alkyl groups attached to an oxygen or sulfur.

The term cycloalkyl refers to saturated rings of 3 to 7 carbon atoms with cyclopentyl and cyclohexyl being most preferred.

The term halogen refers to chloro, bromo and fluoro.

The term hal substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The symbols

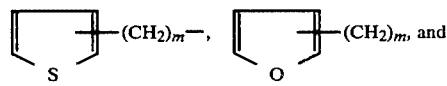

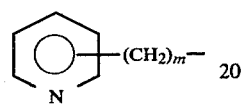

represent that the alkylene bridge is attached to an available carbon atom.

The compounds of formula I may be prepared by coupling a phosphinyl acetic or propionic acid of the formula

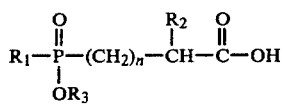

with the imino acid ester of the formula

HX                                                     (III)

wherein $R_3$ is preferably a lower alkyl group such as ethyl, benzyl, or benzhydryl and $R_4$ is preferably an ester such as benzyl. Following completion of the reaction, the $R_3$ and $R_4$ ester group may be removed to yield the corresponding diacid products, i.e., $R_3$ and $R_4$ are both hydrogen, of formula I.

The above coupling reaction can be accomplished using known amide bond forming procedures. For example, the reaction can be performed in the presence of a coupling agent such as carbonyldiimidazole, dicyclohexylcarbodiimide, etc., or the acid of formula II can be activated by formation of its mixed anhydride, symmetrical anhydride, acid halide (preferably acid chloride), or acid ester, or by use of Woodward reagent K, N-ethoxycarbonyl-2-ethoxy-1,2-dihydroisoquinoline, or the like. A review of these methods can be found in *Methoden der Organischen Chemie* (Houben-Weyl), Vol. XV, part II, page 1 et seq. (1974).

The phosphinylalkanoyl imino acids of formula I wherein n is 1 can alternatively be prepared by reacting a compund of formula III with a pholane having the formula

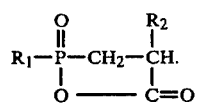

The reaction proceeds most readily when run in the presence of an organic base, e.g., triethylamine, pyridine, N,N-dimethylaniline or the like, in an inert organic solvent such as acetonitrile, dichloromethane, ether, tetrahydrofuran, or the like.

Phosphinyl-acetic or propionic acid derivatives of formula II can be prepared using known procedures; see, for example, U.S. Pat. No. 4,168,267, issued Sept. 18, 1979. Phospholanes of formula IV can be prepared following the procedures described in Zh. Obsh. Kim., 37:411 (1967) and Zh. Obsh. Kim., 38:288 (1968).

The products of formula I wherein either or both of $R_3$ and $R_4$ are lower alkyl, benzyl, or benzhydryl can be hydrogenated, for example, by treating with hydrogen in the presence of a palladium on carbon catalyst or chemically treated such as with sodium hydroxide in aqueous dioxane or with trimethylsilylbromide in dichloromethane to yield the products of formula I wherein $R_3$ and $R_4$ are hydrogen.

The ester products of formula I wherein $R_4$ is

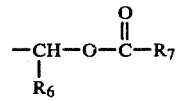

may be obtained by employing the imino acid of formula III in the above reactions with the ester group already in place. Such ester reactants can be prepared by treating the imino acid with the acid chloride such as

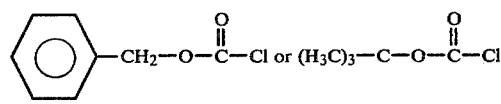

so as to protect the N-atom. The protected acid compound is then reacted in the presence of a base with a compound of the formula

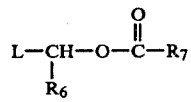

wherein L is a leaving group such as chlorine, bromine, tolylsulfonyl, etc., followed by removal of the N-protecting group such as by treatment with acid or hydrogenation.

The ester products of formula I wherein $R_4$ is

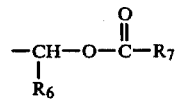

can also be obtained by treating the product of formula I wherein $R_4$ is hydrogen with a molar equivalent of the compound of formula V. The diester products wherein $R_3$ and $R_4$ are the same and are

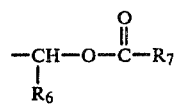

can be obtained by treating the product of formula I wherein $R_3$ and $R_4$ are both hydrogen, an alkali metal or tetraalkyl ammonium salt with two or more equivalents of the compound of formula V.

The ester products of formula I wherein $R_3$ is $$-\underset{\underset{R_6}{|}}{CH}-O-\underset{\underset{}{\overset{O}{\|}}}{C}-R_7$$

can be obtained by treating the product of formula I wherein $R_3$ is hydrogen, an alkali metal or tetraalkyl ammonium salt and $R_4$ is benzyl or benzhydryl with the compound of formula V in the presence of base. Removal of the $R_4$ ester group such as by hydrogenation yields the products of formula I wherein $R_3$ is $$-\underset{\underset{R_6}{|}}{CH}-O-\underset{\underset{}{\overset{O}{\|}}}{C}-R_7$$

and $R_4$ is hydrogen.

Preferred compounds of this invention are those wherein
X is $R_4$ is hydrogen, an alkali metal salt, or $$-\underset{\underset{R_6}{|}}{CH}-O-\underset{\underset{}{\overset{O}{\|}}}{C}-R_7,$$

$R_6$ is hydrogen, straight or branched chain lower alkyl of 1 to 4 carbons, or cyclohexyl and $R_7$ is a straight or branched chain lower alkyl of 1 to 4 carbons or phenyl, especially hydrogen, $$\underset{\underset{}{|}}{\overset{CH_3}{|}}\underset{}{\overset{}{}}\underset{}{\overset{O}{\|}}\quad\underset{\underset{}{|}}{\overset{CH(CH_3)_2}{|}}\underset{}{\overset{O}{\|}}$$
$$-CH-O-C-CH_3, -CH-\phantom{O}-O-C-C_2H_5,$$

$$-\underset{\underset{CH_3}{|}}{CH}-O-\overset{O}{\overset{\|}{C}}-C_2H_5, -CH_2-O-\overset{O}{\overset{\|}{C}}-C(CH_3)_3, \text{ or an}$$

alkali metal salt.
$R_2$ is hydrogen.
n is zero.
$R_3$ is hydrogen, an alkali metal salt, lower alkyl of 1 to 4 carbons, benzyl, or $$-\underset{\underset{R_6}{|}}{CH}-O-\overset{O}{\overset{\|}{C}}-R_7$$

wherein $R_6$ is hydrogen, straight or branched chain lower alkyl of 1 to 4 carbons, or cyclohexyl, and $R_7$ is straight or branched chain lower alkyl of 1 to 4 carbons or phenyl, especially hydrogen, alkali metal salt, ethyl, $$-\underset{\underset{CH_3}{|}}{CH}-O-\overset{O}{\overset{\|}{C}}-CH_3, -\underset{\underset{CH_3}{|}}{CH}-O-\overset{O}{\overset{\|}{C}}-C_2H_5,$$

$$-CH_2-O-\overset{O}{\overset{\|}{C}}C(CH_3)_3 \text{ or } -\underset{\underset{CH(CH_3)_2}{|}}{CH}-O-\overset{O}{\overset{\|}{C}}-C_2H_5.$$

$R_1$ is alkyl of 1 to 10 carbons, cycloalkyl—$(CH_2)_m$— wherein cycloalkyl is 5 or 6 carbons, wherein m is zero or an integer from 1 to 4, and $R_5$ is hydrogen, methyl, methoxy, methylthio, chloro, bromo, fluoro, or hydroxy, especially The compounds of this invention wherein at least one of $R_3$ or $R_4$ is hydrogen, form basic salts with various inorganic and organic bases which are also within the scope of the invention. Such salts include ammonium salts, alkali metal salts like lithium, sodium and potassium salts (which are preferred), alkaline earth metal salts like calcium and magnesium salts, salts with organic bases, e.g., dicyclohexylamine salt, benzathine, N-methyl-D-glucamine, hydrabamine salts, salts with amino acids like arginine, lysine and the like. The non-toxic, physiologically acceptable salts are preferred, although other salts are also useful, e.g., in isolating or purifying the product. The salts are formed using conventional techniques.

As shown above, the imino acid or ester portion of the molecule of the products of formula I represented by X is in the L-configuration. An asymmetric center is also present in the phosphinylalkanoyl sidechain when $R_2$ is other than hydrogen. Thus, some of the compounds can accordingly exist in diastereoisomeric forms or in mixtures thereof. The above described processes can utilize racemates, enantiomers or diastereomers as starting materials. When diastereomeric products are prepared, they can be separated by conventional chromatographic or fractional crystallization methods.

The compounds of formula I, and the physiologically acceptable salts thereof, are hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglubulin in blood pressure, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→angiotensin I→angiotensin II sequence by inhibiting angiotensin converting enzyme and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided in a basis of about 0.1 to 100 mg. per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 330 mg. of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methylclothiazide, trichloromethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 10 to 500 mg. of a compound of formula I is compounded with physiologically acceptable vehicle, carrier, excipient, binder, preservative, stabilizer, flavor, etc. in a unit dosage form as called for by accepted pharmaceutical practice. The amount of active substance in these compositions or preparations is such that a suitable dosage in the range indicated is obtained.

The following examples are illustrative of the invention. Temperatures are given in degrees centigrade. AG-50W-X8 refers to a crosslinked polystyrene divinylbenzene sulfonic acid cation exchange resin. HP-20 refers to a porous crosslinked polystyrene-divinyl benzene polymer resin.

EXAMPLE 1

(S)-1,2,3,4-Tetrahydro-2-[[hydroxy(4-phenylbutyl)-phosphinyl]acetyl]-3-isoquinolinecarboxylic acid, dilithium salt (a) (4-Phenylbutyl)phosphonous acid, diethyl ester Magnesium metal (4.8 g., 0.2 mole) was slurried in 50 ml. of diethyl ether and a solution of 1-chloro-4-phenylbutane (36.4 g., 0.22 mole) in 100 ml. of diethyl ether was added dropwise at a rate to maintain gentle reflux, followed by stirring at reflux for one hour. After cooling, and filtration under argon, the Grignard solution (0.147 mole by titration) was added dropwise to a chilled (0°) solution of diethylchlorophosphite (25.7 g., 0.16 mole) in 100 ml. of ether, at a rate to maintain the internal temperature at 0°–10°. Following the addition, the mixture was heated at reflux for 1.5 hours. After filtration and concentration at atmospheric pressure, under argon, the residue was fractionated at reduced pressure to give 29.7 g. of (4-phenylbutyl)phosphonous acid, diethyl ester; b.p. 110°–113° at 0.09–0.1 mm.

(b) [Ethoxy(4-phenylbutyl)phosphinyl]acetic acid, methyl ester

A mixture of 16.9 g. (0.11 mole) of methyl bromoacetate and 5.0 g. (0.019 mole) of (4-phenylbutyl)phosphonous acid, diethyl ester was heated on a 140°–150° oil bath until distillation of ethyl bromide was detected. An additional 16 g. (0.063 mole) of (4-phenylbutyl)phosphonous acid, diethyl ester was then gradually added to the reaction mixture. Heating was then continued for 45 minutes. After cooling to 100°, excess reagent was removed in vacuo to give 25 g. of crude product ($R_f$=0.25 silica gel/ethyl acetate). Impurities with higher $R_f$ values were separated by flash chromatography using ethyl acetate. As a result, 18.3 g. of [ethoxy(4-phenylbutyl)phosphinyl]acetic acid, methyl ester were obtained.

(c) [Ethoxy(4-phenylbutyl)phosphinyl]acetic acid

A solution of 15 g. (0.05 mole) of [ethoxy(4-phenylbutyl)phosphinyl]acetic acid, methyl ester in 51 ml. of 0.99 N sodium hydroxide (0.05 mole) was stirred for 30 minutes at room temperature. After extraction with ether, the solution was treated with 8.5 l. of 5 N hydrochloric acid. The product was extracted into ethyl acetate, dried and the solvent evaporated in vacuo to give 13.6 g. of [ethoxy(4-phenylbutyl)phosphinyl]acetic acid as an oil product. $R_f$=0.75 on silica gel using dichloromethane/acetic acid/methanol (8:1:1).

(d) 1,2,3,4-Tetrahydro-3-isoquinolinecarboxylic acid, phenylmethyl ester, p-toluenesulfonic acid salt A mixture of (S)-1,2,3,4-tetrahydro-3-isoquinolinecarboxylic acid (26.1 g., 147 mmole), benzyl alcohol (78 ml., 750 mmole), p-toluenesulfonic acid monohydrate (34.5 g., 181 mmole) and 450 ml. of toluene was refluxed for 5 hours while the resulting water was removed using a Dean-Stark trap. After cooling, the solvent was removed at reduced pressure. Ether was added to the residue and the white precipitate was filtered. This was recrystallized from aqueous methanol (1:1) to give 45.6 g. of 1,2,3,4-tetrahydro-3-isoquinolinecarboxylic acid, phenylmethyl ester, p-toluenesulfonic acid salt as a white powder; $[\alpha]_D^{20}$= −50.2° (c=1, methanol); m.p. 146°.

(e) (S)-1,2,3,4-Tetrahydro-2-[[ethoxy(4-phenylbutyl)phosphinyl]acetyl]-3-isoquinolinecarboxylic acid, phenylmethyl ester A mixture of [ethoxy(4-phenylbutyl)-phosphinyl]acetic acid (2.0 g., 7.0 mmole), acetonitrile (20 ml.), and carbonyldiimidazole (1.0 g., 10. eq.) was stirred at 0° (ice bath) in an argon atmosphere for one hour. The ice bath was removed and the reaction mixture was treated with 1,2,3,4-tetrahydro-3-isoquinolinecarboxylic acid, phenylmethyl ester, p-toluenesulfonic acid salt (3.1 g., 1.0 eq.) and triethylamine (1.0 ml., 1.0 eq.). After 16 hours, the acetonitrile was stripped and the residue was taken up in ethyl acetate. The ethyl acetate was washed with saturated sodium bicarbonate, 5% potassium bisulfate, water, brine, dried (MgSO$_4$), and evaporated. The residue (3.5 g.) was chromatographed on silica (120 g.) eluting with 2:1 hexane/acetone to give 2.0 g. (3.7 mmole) of (S)-1,2,3,4-tetrahydro-2-[[ethoxy(4-phenylbutyl)phosphinyl]acetyl]-3-isoquinolinecarboxylic acid, phenylmethyl ester as an oil. Tlc (3:2 hexane/acetone) single spot at R$_f$=0.4.

(f) (S)-1,2,3,4-Tetrahydro-2-[[ethoxy(4-phenylbutyl)phosphinyl]acetyl]-3-isoquinolinecarboxylic acid A mixture of the diester product from part (e) (2.0 g., 3.7 mmole), methanol, and 10% palladium on carbon catalyst was hydrogenated on the Parr apparatus at 50 psi for two hours. The catalyst was removed by filtration (Celite bed) and the solvent stripped to yield 1.6 g. (3.6 mmole) of (S)-1,2,3,4-tetrahydro-2-[[ethoxy(4-phenylbutyl)phosphinyl]acetyl]-3-isoquinolinecarboxylic acid as an oil. Tlc (100:5:5 dichloromethane/methanol/acetic acid) single spot at R$_f$=0.6.

(g) (S)-1,2,3,4-Tetrahydro-2-[[hydroxy(4-phenylbutyl)phosphinyl]acetyl]-3-isoquinolinecarboxylic acid, dilithium salt The mono ester product from part (f) (1.6 g., 3.6 mmole) in dry dichloromethane (10 ml.) was treated with trimethylsilylbromide (1.5 ml., 3.0 eq.) at 25° in an argon atmosphere. After 16 hours the dichloromethane and excess trimethylsilylbromide were removed in vacuo. The residue was taken in ethyl acetate and water and stirred for 5 minutes. The phases were separated and the ethyl acetate portion was washed with brine, dried (MgSO$_4$), and evaporated. The residue (1.5 g.) was taken up in 1 N lithium hydroxide (7.0 ml., 2.0 eq.) and chromatographed on an HP-20 (200 ml.) column eluting with a linear gradient water→acetonitrile (0→90%). The desired fractions were combined, filtered (millipore), and lyophilized to yield 1.1 g. (2.6 mmole) of (S)-1,2,3,4-tetrahydro-2-[[hydroxy(4-phenylbutyl)phosphinyl]acetyl]-3-isoquinolinecarboxylic acid, dilithium salt as a white solid, m.p. 234°–236° (dec.). Tlc (7:2:1) isopropanol/conc. NH$_4$OH/water) single spot at R$_f$=0.7, [α]$_D$=+5.2° (c=10 mg./ml., CH$_3$OH), [α]$_{365}$=−41.6°, (c=10 mg./ml., CH$_3$OH).

Anal. Calc'd. for C$_{22}$H$_{24}$NO$_5$P.2Li.2H$_2$O: C, 56.78; H, 6.06; N, 3.01; P, 6.6. Found: C, 56.84; H, 5.79; N, 2.92; P, 6.5.

EXAMPLES 2–18

Following the procedure of Example 1 but employing the phosphinyl acid shown in Col. I and the imino acid ester shown in Col. II one obtains the product shown in Col. III.

Col. I $$R_1-\underset{\underset{OR_3}{|}}{\overset{\overset{O}{\|}}{P}}-(CH_2)_n-\underset{\underset{}{|}}{\overset{\overset{R_2}{|}}{CH}}-COOH$$

Col. II

HX

Col. III $$R_1-\underset{\underset{OR_3}{|}}{\overset{\overset{O}{\|}}{P}}-(CH_2)_n-\underset{\underset{}{|}}{\overset{\overset{R_2}{|}}{CH}}-\overset{\overset{O}{\|}}{C}-X$$

| Example | R$_1$ | R$_3$ | n | R$_2$ | X |
|---|---|---|---|---|---|
| 2 | ⟨O⟩—(CH$_2$)$_2$— | —C$_2$H$_5$ | zero | —H | 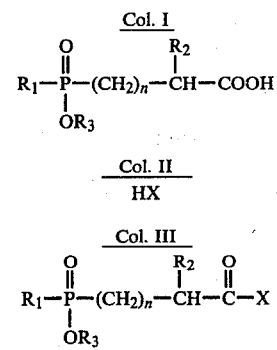 -N⟶COOCH$_2$—⟨O⟩  H (L) |
| 3 | ⟨O⟩—(CH$_2$)$_4$— | —C$_2$H$_5$ | zero | —H | -N⟶COOCH$_2$—⟨O⟩  H (L) |

-continued
| Example | R₁ | R₃ | n | R₂ | X |
|---|---|---|---|---|---|
| 4 | H₃C—(CH₂)₆— | —C₂H₅ | one | —CH₃ | 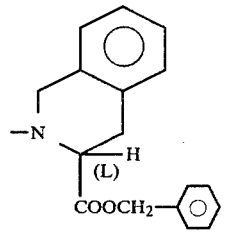 |
| 5 | 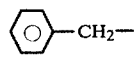 | —C₂H₅ | zero | —C₂H₅ | 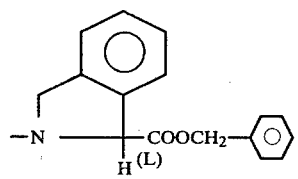 |
| 6 | 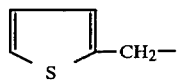 | —CH—(C₆H₅)₂ | zero | —H | 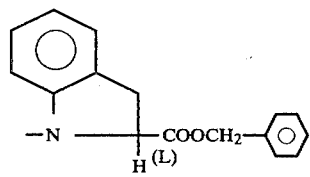 |
| 7 | 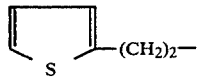 | —C₂H₅ | one | —H | 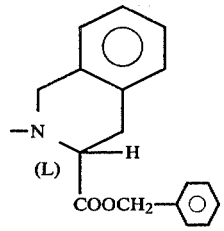 |
| 8 | 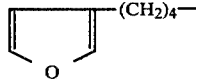 | —CH₂—C₆H₅ | zero | —H | 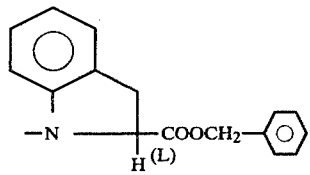 |
| 9 | 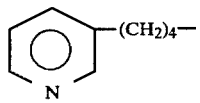 | —C₂H₅ | one | —CH₂—C₆H₅ | 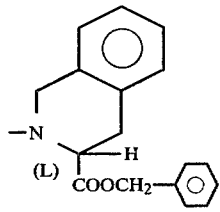 |
| 10 | 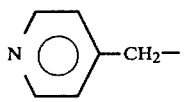 | —C₂H₅ | one | —(CH₂)₂—C₆H₅ | 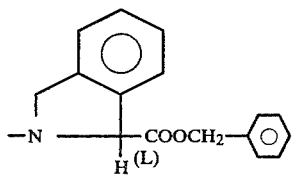 |

-continued

| Example | R₁ | R₃ | n | R₂ | X |
|---|---|---|---|---|---|
| 11 | F₃C—CH₂— | —C₂H₅ | zero | —H | benzyl-fused bicyclic with —N—CH(COOCH₂Ph)—H (L) |
| 12 | H₃C—C₆H₄— | —C₂H₅ | zero | —H | benzyl-fused bicyclic with —N—CH(COOCH₂Ph)—H |
| 13 | 3,4-(H₃CO)₂C₆H₃—(CH₂)₂— | —C₂H₅ | zero | —H | benzyl-fused bicyclic with —N—CH(COOCH₂Ph)—H (L) |
| 14 | Cl—C₆H₄—(CH₂)₃— | —C₂H₅ | zero | —H | benzyl-fused bicyclic with —N—CH(COOCH₂Ph)—H (L) |
| 15 | C₆H₅—(CH₂)₄— | —C₂H₅ | zero | —H | benzyl-fused bicyclic with —N—CH(H)(L)—COOCH(C₂H₅)—C(O)—CH₃ |
| 16 | C₆H₅—(CH₂)₂— | —C₂H₅ | zero | —H | benzyl-fused bicyclic with —N—CH(H)(L)—COOCH(CH(CH₃)₂)—C(O)—C₂H₅ |

-continued

| Example | R₁ | R₃ | n | R₂ | X |
|---|---|---|---|---|---|
| 17 | (thiophene)-CH₂— | —C₂H₅ | zero | —H | —N—(CH with phenyl-CH₂)—COOCH₂—C(=O)—O—phenyl, H(L) |
| 18 | (pyridine)-(CH₂)₄— | —C₂H₅ | zero | —H | —N—(CH with phenyl-CH₂)—COO—[phthalide-like], H(L) |

The diester products shown in Col. III of Examples 2 to 14 would be treated to remove both R₃ and R₄ ester groups and yield the corresponding diacid. The ester products shown in Col. III of Examples 15 to 18 would be treated to remove only the R₃ ester group and yield the corresponding monoester product.

EXAMPLE 19

(S)-1,2,3,4-Tetrahydro-2-[[[(2,2-dimethyl-1-oxopropoxy)methoxy](4-phenylbutyl)phosphinyl]-acetyl]-3-isoquinolinecarboxylic acid (a) (S)-1,2,3,4-Tetrahydro-2-[[hydroxy(4-phenylbutyl)phosphinyl]acetyl]-3-isoquinolinecarboxylic acid, phenylmethyl ester A solution of (S)-1,2,3,4-tetrahydro-2-[[ethoxy(4-phenylbutyl)phosphinyl]acetyl]-3-isoquinolinecarboxylic acid, phenylmethyl ester (1.07 g., 2.0 mmole) from Example 1(e) in dry dichloromethane (5 ml.) is treated with bromotrimethylsilane (0.4 ml., 3 mmole) and stirred at room temperature under argon for 16 hours. The mixture is evaporated to dryness and the residue is partitioned between ethyl acetate-water. The ethyl acetate phase is washed with saturated sodium chloride solution, dried (Na₂SO₄) and evaporated to give (S)-1,2,3,4-tetrahydro-2-[[hydroxy(4-phenylbutyl)phosphinyl]-acetyl]-3-isoquinolinecarboxylic acid, phenylmethyl ester.

(b) (S)-1,2,3,4-Tetrahydro-2-[[[(2,2-dimethyl-1-oxopropoxy)methoxy](4-phenylbutyl)phosphinyl]acetyl]-3-isoquinolinecarboxylic acid, phenylmethyl ester Triethylamine (2 eq.) and chloromethyl pivalate (2 eq.) are added to a solution of (S)-1,2,3,4-tetrahydro-2-[[hydroxy(4-phenylbutyl)-phosphinyl]acetyl]-3-isoquinolinecarboxylic acid, phenylmethyl ester in dimethylformamide under an argon atmosphere and the resulting mixtute is stirred at room temperature for several hours. The reaction mixture is diluted with ethyl acetate, washed with water, brine, dried (MgSO₄), and evaporated. The crude product is chromatographed on silica gel to give (S)-1,2,3,4-2-[[[(2,2-dimethyl-1-oxopropoxy)methoxy](4-phenylbutyl)phosphinyl]acetyl]-3-isoquinolinecarboxylic acid, phenylmethyl ester.

(c) (S)-1,2,3,4-Tetrahydro-2-[[[(2,2-dimethyl-1-oxopropoxy)methoxy](4-phenylbutyl)phosphinyl]acetyl]-3-isoquinolinecarboxylic acid A solution of the diester product from part (b) in methanol is added to a 10% palladium on carbon catalyst and the resulting mixture is shaken in a Parr hydrogenation apparatus for several hours. The catalyst is filtered off and the methanol stripped from the filtrate. The crude product is chromatographed on silica gel to yield (S)-1,2,3,4-tetrahydro-2-[[[(2,2-dimethyl-1-oxopropoxy)methoxy](4-phenylbutyl)-phosphinyl]acetyl]-3-isoquinolinecarboxylic acid.

EXAMPLES 20-24

Following the procedure of Example 19 but employing the alkylating agent shown in Col. I in place of the chloromethyl pivalate, one obtains the product listed in Col. II.

| Example | Col. I | Col. II |
|---|---|---|
| 20 | Br—CH₂—O—C(=O)—CH₃ | (S)—1,2,3,4-tetrahydro-2-[[[(acetyloxy)methoxy]-(4-phenylbutyl)-phosphinyl]acetyl]-3-isoquinolinecarboxylic acid |
| 21 | Cl—CH(CH₃)—O—C(=O)—OC₂H₅ | (S)—1,2,3,4-tetrahydro-2-[[[1-(ethoxycarbonyloxy)ethoxy]-(4-phenylbutyl)-phosphinyl]acetyl]-3-isoquinolinecarboxylic acid |
| 22 | Br-(3-oxo-1-isobenzofuranyl) | (S)—1,2,3,4-tetrahydro-2-[[(3-oxo-1-isobenzofuranyloxy)-(4-phenylbutyl)-phosphinyl]acetyl]-3-isoquinolinecarboxylic acid |

-continued

| Example | Col. I | Col. II |
|---|---|---|
| 23 | ClCH₂—O—C(=O)—C₆H₅ | (S)—1,2,3,4-tetrahydro-2-[[[(benzoyloxy)methoxy]-(4-phenylbutyl)-phosphinyl]acetyl]-3-isoquinolinecarboxylic acid |
| 24 | Cl—CH(CH(CH₃)₂)—O—C(=O)—C₂H₅ | (S)—1,2,3,4-tetrahydro-2-[[[2-methyl-1-(1-oxopropoxy)-propoxy](4-phenylbutyl)phosphinyl]acetyl]-3-isoquinolinecarboxylic acid |

EXAMPLE 25

(S)-1,2,3,4-Tetrahydro-2-[[hydroxy(4-phenylbutyl)-phosphinyl]acetyl]-3-isoquinolinecarboxylic acid, disodium salt Following the procedure of Example 1 but employing AG-50W-X8 (Na+) resin in part (g), one obtains (S)-1,2,3,4-tetrahydro-2-[[hydroxy-(4-phenylbutyl)-phosphinyl]acetyl]-3-isoquinolinecarboxylic acid, disodium salt.

This procedure can be employed in Examples 2–24 to give the corresponding mono or disodium salt. Similarly, by employing a potassium resin the corresponding mono or dipotassium salt is obtained.

EXAMPLE 26

1000 tablets each containing the following ingredients:

| | |
|---|---|
| (S)—1,2,3,4-Tetrahydro-2-[[hydroxy(4-phenylbutyl)-phosphinyl]-3-isoquinolinecarboxylic acid, disodium salt | 100 mg. |
| Corn starch | 50 mg. |
| Gelatin | 7.5 mg. |
| Avicel (microcrystalline cellulose) | 25 mg. |
| Magnesium stearate | 2.5 mg. |
| | 185 mg. | are prepared from sufficient bulk quantities by mixing the (S)-1,2,3,4-tetrahydro-2-[[hydroxy-(4-phenylbutyl)-phosphinyl]acetyl]-3-isoquinolinecarboxylic acid, disodium salt and corn starch with an aqueous solution of the gelatin. The mixture is dried and ground to a fine powder. The Avicel and then the magnesium stearate are admixed with granulation. This mixture is then compressed in a tablet press to form 1000 tablets each containing 100 mg. of active ingredient.

In a similar manner, tablets containing 100 mg. of the product of any of Examples 1 to 24 can be prepared.

Similarly, the above procedure can be employed with a variation of the amounts of ingredients to produce tablets containing 50 mg. of active compound.

EXAMPLE 27

An injectable solution is prepared as follows:

| | |
|---|---|
| (S)—1,2,3,4-Tetrahydro-2-[[hydroxy(4-phenylbutyl)-phosphinyl]acetyl]-3-isoquinolinecarboxylic acid, disodium salt | 500 g. |
| Methyl paraben | 5 g. |
| Propyl paraben | 1 g. |
| Sodium chloride | 25 g. |
| Water for injection | 5 l |

The active substance, preservatives, and sodium chloride are dissolved in 3 liters of water for injection and then the volume is brought up to 5 liters. The solution is filtered through a sterile filter and aseptically filled into presterilized vials which are closed with presterilized rubber closures. Each vial contains 5 ml. of solution in a concentration of 100 mg. of active ingredient per ml. of solution for injection.

In a similar manner, an injectable solution containing 100 mg. of active ingredient per ml. of solution can be prepared for the product of any Examples 1 to 24.

EXAMPLE 28

1000 tablets each containing the following ingredients:

| | |
|---|---|
| (S)—1,2,3,4-Tetrahydro-2-[[hydroxy(4-phenylbutyl)-phosphinyl]acetyl]-3-isoquinolinecarboxylic acid, disodium salt | 100 mg. |
| Avicel | 100 mg. |
| Hydrochlorothiazide | 12.5 mg. |
| Lactose | 113 mg. |
| Corn starch | 17.5 mg. |
| Stearic acid | 7 mg. |
| | 350 mg. | are prepared from sufficient bulk quantities by slugging the (S)-1,2,3,4-tetrahydro-2-[[hydroxy-(4-phenylbutyl)-phosphinyl]acetyl]-3-isoquinolinecarboxylic acid, disodium salt, Avicel and a portion of the stearic acid. The slugs are ground and passed through a #2 screen, then mixed with the hydrochlorothiazide, lactose, corn starch, and remainder of the stearic acid. The mixture is compressed into 350 mg. capsule shaped tablets in a tablet press. The tablets are scored for dividing in half.

In a similar manner, tablets can be prepared containing 100 mg. of the product of any of Examples 1 to 24.

What is claimed is:

1. A compound of the formula

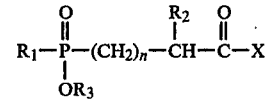

and a pharmaceutically acceptable salt thereof wherein X is

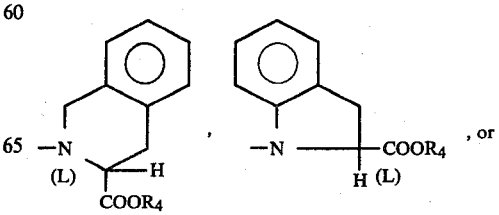

-continued

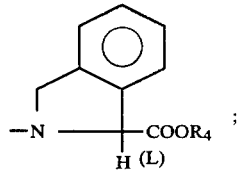

R₁ is straight or branched chain alkyl of 1 to 10 carbons, halo substituted lower alkyl wherein lower alkyl is straight or branched chain of 1 to 7 carbons, cycloalkyl-(CH₂)$_m$— wherein cycloalkyl is a saturated ring of 3 to 7 carbon atoms,

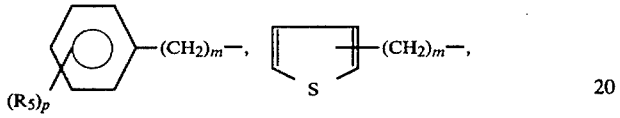

R₂ is hydrogen, straight or branched chain lower alkyl of 1 to 7 carbons, halo substituted lower alkyl wherein lower alkyl is straight or branched chain of 1 to 7 carbons, benzyl, or phenethyl;

R₃ and R₄ are independently selected from the group consisting of hydrogen, straight or branched chain lower alkyl of 1 to 7 carbons, benzyl, benzhydryl, and

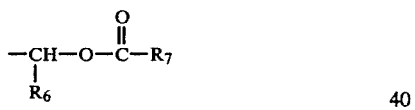

wherein R₆ is hydrogen, straight or branched chain alkyl of 1 to 10 carbons, cycloalkyl which is a saturated ring of 3 to 7 carbon atoms, or phenyl, and R₇ is hydrogen, straight or branched chain alkyl of 1 to 10 carbons, cycloalkyl which is a saturated ring of 3 to 7 carbon atoms, lower alkoxy of 1 to 7 carbons, phenyl, benzyl, phenethyl, or R₆ and R₇ taken together are —(CH₂)₂—, —(CH₂)₃—, —CH=CH—, or

n is zero to one;
m is zero or an integer from 1 to 7;
R₅ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy; and
p is one, two or three provided that p is more than one only if R₅ is hydrogen, methyl, methoxy, chloro, or fluoro.

2. A compound of claim 1 wherein
X is

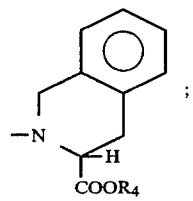

R₂ is hydrogen;
n is zero;
R₃ is hydrogen, an alkali metal salt, lower alkyl of 1 to 4 carbons, benzyl, or

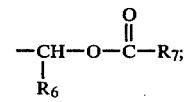

R₄ is hydrogen, an alkali metal salt, or

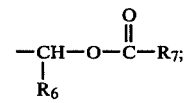

R₆ is hydrogen, straight or branched chain lower alkyl of 1 to 4 carbons, or cyclohexyl;
R₇ is straight or branched chain lower alkyl of 1 to 4 carbons or phenyl;
R₁ is alkyl of 1 to 10 carbons,

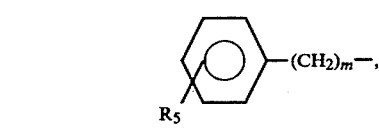

cycloalkyl—(CH₂)$_m$— wherein cycloalkyl is a saturated ring of 5 or 6 carbons,

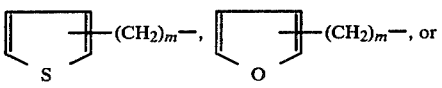

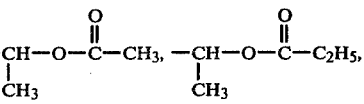

m is zero or an integer from 1 to 4; and
R₅ is hydrogen, methyl, methoxy, methylthio, chloro, bromo, fluoro, or hydroxy.

3. A compound of claim 2 wherein
R₃ is hydrogen, alkali metal salt, ethyl $$-\underset{\underset{CH_3}{|}}{CH}-O-\underset{\underset{}{\overset{O}{\|}}}{C}-CH_3, -\underset{\underset{CH_3}{|}}{CH}-O-\underset{\underset{}{\overset{O}{\|}}}{C}-C_2H_5,$$

-continued

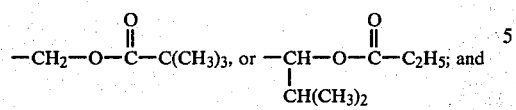

R₄ is hydrogen, alkali metal salt,

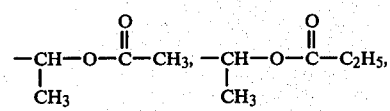

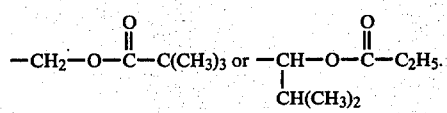

4. A compound of claim 3 wherein R₁ is

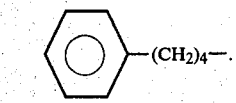

5. The compound of claim 4 wherein $R_3$ and $R_4$ are hydrogen.

6. The compound of claim 4 wherein $R_3$ and $R_4$ are an alkali metal salt.

7. A composition useful for treating hypertension comprising a pharmaceutically acceptable carrier and an effective amount of a hypotensive agent or pharmaceutically acceptable salt thereof of the formula

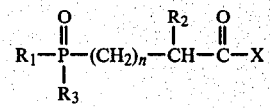

wherein X, $R_1$, $R_2$, $R_3$, and n are as defined in claim 1.

8. The composition of claim 7 also including a diuretic.

9. The method of alleviating hypertension in a mammalian specie which comprises administering an effective amount of the composition of claim 7.

* * * * *

UNITED STATES PATENT AND TRADEMARK OFFICE
CERTIFICATE OF CORRECTION

PATENT NO. : 4,427,665
DATED : January 24, 1984
INVENTOR(S) : Donald S. Karanewsky et al.

It is certified that error appears in the above-identified patent and that said Letters Patent are hereby corrected as shown below:

Column 3, line 5, delete "hal" and insert -- halo -- .
Column 8, line 47, delete "8.5 1" and insert -- 8.5 ml. -- .
Column 11, Example 5, under $R_1$ the formula should read

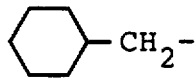

Signed and Sealed this

Twenty-ninth Day of October 1985

[SEAL]

Attest:

DONALD J. QUIGG

Attesting Officer

Commissioner of Patents and Trademarks—Designate